(12) United States Patent
Kuzma et al.

(10) Patent No.: US 9,120,249 B2
(45) Date of Patent: *Sep. 1, 2015

(54) IMPLANT DEVICE RELEASE AGENTS AND METHODS OF USING SAME

(75) Inventors: Petr Kuzma, Princeton, NJ (US); Stephanie Decker, Princeton, NJ (US); Harry Quandt, Bensalem, PA (US)

(73) Assignee: ENDO PHARMACEUTICALS SOLUTIONS INC., Malvern, PA (US)

( * ) Notice: Subject to any disclaimer, the term of this patent is extended or adjusted under 35 U.S.C. 154(b) by 910 days.

This patent is subject to a terminal disclaimer.

(21) Appl. No.: 12/109,852

(22) Filed: Apr. 25, 2008

(65) Prior Publication Data

US 2008/0311170 A1 Dec. 18, 2008

Related U.S. Application Data

(60) Provisional application No. 60/914,511, filed on Apr. 27, 2007.

(51) Int. Cl.
*B29C 33/62* (2006.01)
*B29C 41/08* (2006.01)
*A61L 27/52* (2006.01)
*A61L 27/54* (2006.01)

(52) U.S. Cl.
CPC ............... *B29C 33/62* (2013.01); *A61L 27/52* (2013.01); *A61L 27/54* (2013.01); *B29C 41/085* (2013.01); *A61L 2300/602* (2013.01); *A61L 2300/802* (2013.01)

(58) Field of Classification Search
None
See application file for complete search history.

(56) References Cited

U.S. PATENT DOCUMENTS

| | | | |
|---|---|---|---|
| 2,513,014 A | 6/1950 | Fields | |
| 3,876,581 A * | 4/1975 | Neogi | 521/62 |
| 3,921,632 A | 11/1975 | Bardani | |
| 4,131,604 A | 12/1978 | Szycher | |
| 4,285,987 A | 8/1981 | Ayer et al. | |
| 4,298,002 A | 11/1981 | Ronel et al. | |
| 4,386,039 A | 5/1983 | Szycher | |
| 4,523,005 A | 6/1985 | Szycher | |
| 4,743,673 A | 5/1988 | Johnston et al. | |
| 4,751,133 A | 6/1988 | Szycher et al. | |
| 4,846,793 A | 7/1989 | Leonard et al. | |
| 4,871,094 A | 10/1989 | Gall et al. | |
| 4,954,587 A | 9/1990 | Mueller | |
| 4,959,217 A | 9/1990 | Sanders et al. | |
| 4,994,028 A | 2/1991 | Leonard et al. | |
| 5,004,614 A | 4/1991 | Staniforth | |
| 5,023,313 A * | 6/1991 | Edwards | 524/166 |
| 5,035,891 A | 7/1991 | Runkel et al. | |
| 5,254,662 A | 10/1993 | Szycher et al. | |
| 5,266,325 A | 11/1993 | Kuzma et al. | |
| 5,273,752 A | 12/1993 | Ayer et al. | |
| 5,292,515 A | 3/1994 | Moro et al. | |
| 5,342,622 A | 8/1994 | Williams et al. | |
| 5,354,835 A | 10/1994 | Blair | |
| 5,431,921 A | 7/1995 | Thombre | |
| 5,468,811 A | 11/1995 | Moro et al. | |
| 5,614,223 A | 3/1997 | Sipos | |
| 5,637,309 A | 6/1997 | Tajima et al. | |
| 5,756,127 A | 5/1998 | Grisoni et al. | |
| 5,817,343 A | 10/1998 | Burke | |
| 5,854,127 A | 12/1998 | Pan | |
| 5,876,761 A | 3/1999 | Bodmer et al. | |
| 6,056,970 A * | 5/2000 | Greenawalt et al. | 424/426 |
| 6,159,490 A | 12/2000 | Deghenghi | |
| 6,313,254 B1 | 11/2001 | Meijs et al. | |
| 6,361,797 B1 | 3/2002 | Kuzma et al. | |
| 6,525,145 B2 * | 2/2003 | Gevaert et al. | 525/450 |
| 2001/0007670 A1 * | 7/2001 | Liu et al. | 424/400 |
| 2003/0162862 A1 * | 8/2003 | McCabe et al. | 523/106 |
| 2003/0219475 A1 * | 11/2003 | Truong-Le | 424/450 |
| 2004/0071736 A1 | 4/2004 | Quinn et al. | |
| 2004/0097419 A1 | 5/2004 | Petersen et al. | |
| 2004/0236416 A1 | 11/2004 | Falotico | |
| 2005/0037078 A1 | 2/2005 | Kuo et al. | |
| 2005/0079216 A1 * | 4/2005 | Petereit et al. | 424/464 |
| 2005/0143303 A1 | 6/2005 | Quay et al. | |
| 2006/0019903 A1 | 1/2006 | Kuzma et al. | |
| 2006/0204540 A1 | 9/2006 | Kuzma et al. | |
| 2007/0037897 A1 * | 2/2007 | Wang et al. | 523/106 |
| 2007/0178156 A1 * | 8/2007 | Brown et al. | 424/472 |
| 2008/0311170 A1 | 12/2008 | Kuzma | |

(Continued)

FOREIGN PATENT DOCUMENTS

| | | |
|---|---|---|
| CN | 1233981 A | 11/1999 |
| EP | 0 246 653 A2 | 11/1987 |

(Continued)

OTHER PUBLICATIONS

Lee et al. Biomaterials 2007 28:2041-2050.*
Dong et al. International Journal of Pharmaceutics 2008 35:166-171; available online Aug. 31, 2007.*
Percell et al. "Nonmetallic fatty chemicals as internal mold release agents in polymers" in Coatings Technology Handbook ed. Tracton. Taylor and Francis:Boca Raton 2006:72-1-72-7.*
Higuchi, et al., *Pro-Drugs as Novel Drug Delivery Systems: A.C.S Symposium Series*, American Chemical Society, Washington, DC, 1975. table of contents only.

(Continued)

*Primary Examiner* — Robert A Wax
*Assistant Examiner* — Caralynne Helm
(74) *Attorney, Agent, or Firm* — RatnerPrestia

(57) ABSTRACT

Medical implant devices are prepared from a polymeric material and a release agent, where the device is a molded, reservoir implant, and the release agent has a molecular weight (MW) of at least 1000. The release agent may be a non-ionic surfactant such as Brij 35, polyoxyetheylene(20)sorbitan trioleate, Tween 20, Tween 80, vitamin E TPGS, and a mixture of any two or more thereof. Hydrated implants may have a surface area of about 500 $mm^2$ or greater.

20 Claims, No Drawings

(56) References Cited

U.S. PATENT DOCUMENTS

2009/0035343 A1 2/2009 Kuzma et al.
2009/0087470 A1 4/2009 Kuzma et al.

FOREIGN PATENT DOCUMENTS

| | | |
|---|---|---|
| EP | 0 314 206 B1 | 5/1989 |
| EP | 0 384 646 A1 | 6/1993 |
| EP | 0 551 699 A1 | 7/1993 |
| EP | 0 645 136 A2 | 3/1995 |
| FR | 821383 A | 12/1937 |
| GB | 1 306 541 A | 2/1973 |
| JP | 05-269759 A | 10/1993 |
| JP | 05-269760 A | 10/1993 |
| JP | 07-097338 A | 4/1995 |
| JP | 07-252166 A | 10/1995 |
| JP | 11-506730 A | 6/1999 |
| JP | 2002-535452 A | 10/2002 |
| NZ | 245383 | 5/1994 |
| WO | WO-96/40049 A1 | 12/1996 |
| WO | WO-9817407 A1 | 4/1998 |
| WO | WO-98/44964 A1 | 10/1998 |
| WO | WO-00/44356 | 8/2000 |
| WO | WO00/72827 | 12/2000 |
| WO | WO-02/49573 A2 | 6/2002 |
| WO | WO-02/078597 A2 | 10/2002 |
| WO | WO03/022321 | 3/2003 |
| WO | WO-2004/071736 A2 | 8/2004 |
| WO | WO-2005/013936 A2 | 2/2005 |
| WO | WO-2005/041873 A2 | 5/2005 |
| WO | WO-2006/099288 A3 | 9/2006 |
| WO | WO-2008/061355 A1 | 5/2008 |
| WO | WO-2008/134475 A2 | 11/2008 |

OTHER PUBLICATIONS

Roche, ed., Bioreversible Carriers in Drug Design: Theory and Application, Pergamon Press, New York, 1987. table of contents only.
Berge, et al., "Pharmaceutical Salts," *Journal of Pharmaceutical Sciences*, vol. 66, No. 1, Jan. 1977, pp. 1-19.
American Peptide Company, Inc., Peptide Catalog 2006-2007, pp. 119, 171, 175, 211, 217, 219, 227, 296, 315, 317 and 329.
Bodmer D., et al: "Factors influencing the release of peptides and proteins from biodegradable parenteral depot systems" Journal of Controlled Release, Elsevier, Amsterdam, NLLNKD-DOI:10.1016/0168-3659(92)90014-1, vol. 21, No. 1-3, Jul. 1, 1992, pp. 129-137, XP025702099 ISSN: 0168-3659 [retrieved on Jul. 1, 1992].
European Search Report for EP/92300394, completed Oct. 5, 1992.
European Search Report for EP/92300395, dispatched Feb. 27, 1995.
European Search Report for EP/00904513, completed Mar. 27, 2003.
International Search Report for PCT/US2009/048475, dated Jun. 1, 2010.
Notice of Allowance for U.S. Appl. No. 12/240,690, mail date Mar. 26, 2010.
Non-final Office Action for U.S. Appl. No. 12/490,979, mail date Sep. 29, 2010.
Non-final Office Action for U.S. Appl. No. 12/490,971, mail date Sep. 14, 2010.
Non-final Office Action for U.S. Appl. No. 11/372,749, mail date Feb. 5, 2008.
Notice of Allowance for U.S. Appl. No. 12/171,999, mail date Mar. 22, 2010.
Final Office Action for U.S. Appl. No. 11/155,822, mail date Jul. 8, 2010.
Office Action for U.S. Appl. No. 07/589,957, mail date Oct. 17, 1991.
Remington's Pharmaceutical Sciences, Osol., A. ed., Mack Publishing Co., (1980). table of contents only.
Supplementary European Search Report for EP/67838004, completed Jun. 23, 2010.
International Preliminary Report on Patentability received for PCT/US2009/048475 dated Jan. 5, 2011.
Notice of Allowance received for U.S. Appl. No. 12/490,979 dated Feb. 4, 2011.
Shi et al., Expert Opin. Drug Deliv., "Current Advances in Sustained-Release Systems for Parenteral Drug Delivery," vol. 2(6), 2005, pp. 1039-1058.
International Search Report (PCT/US2009/048475) dated Jun. 1, 2010.
O'Donnell, et al "Therapeutic Potential of a Long Acting Somatostatin Analogue in Gastrointestinal Diseases" GUT, 1989, vol. 30, pp. 1165-1172.
Prommer, "Established and Potential Therapeutic Applications of Octreotide in Palliative Care", Support Care Cancer, 2008, vol. 16, pp. 1117-1123.
Spitz, et al. "GnRH Superanalog Implants for Prostate Cancer" Proceedings of the 12th International Congress of Endocrinology, 2004, pp. 389-395.
U.S. Appl. No. 12/171,999 dated Mar. 22, 2010.
Patent Examination Report Issued for Australian Patent Application No. 2008245710 dated Jul. 16, 2013.
Office Action Issued for Mexican Patent Application No. MX/a/2009/016641 Dated Jun. 18, 2013 (with English language translation).
Office Action Issued for Japanese Application No. 2010-506506 dated Apr. 3, 2013.
Examination Report for Application No. 08746857.5-1455 dated Apr. 11, 2013.
Third Office Action Issued for Chinese Application No. 200880020570.X dated Feb. 26, 2013.
Office Action with Search Report Issued for Taiwan Patent Application No. 97115262 Dated Aug. 16, 2013.
Australian Application Serial No. 2008245710, Examination Report issued Jul. 27, 2012.
Chinese Application Serial No. 200880020570, Chinese Search Report dated Sep. 24, 2012.
Chinese Application Serial No. 200880020570, Second Office Action dated Sep. 27, 2012 (w/English language translation).
Israeli Application Serial No. 201734, Notification of Defects in Patent Application dated Sep. 10, 2012 (w/English language translation).
Office Action Issued for Japanese Pat. App. No. 2010-506506 dated Dec. 10, 2013 (with English language translation).
Korean Office Action, Appl. No. 10-2009-7023460, dated May 28, 2014.
Office Action Issued by the Canadian Intellectual Property Office for Application No. 2,685,397 Dated Jul. 29, 2014.
U.S. Appl. No. 12/490,971, filed Jun. 24, 2009, Kuzma et al.
U.S. Appl. No. 12/490,979, filed Jun. 24, 2009, Kuzma et al.
"RxMed: Pharmaceutical Information-Sandostatin LAR DEPOT" [online], Jan. 6, 2003 [retrieved Aug. 6, 2006]; http://www.rxmed.com.
A.R. Gennaro, Remington: The Science and Practice of Pharmacy, 19th Edition, 1975, pp. 702-703.
Bevan et al., Primary Medical Therapy for Acromegaly: An Open, Prospective, Multicenter Study of the Effects of Subcutaneous and Intramuscular Slow-Release Octreotide on Growth Hormone, Insulin-Like Growth Factor-L, and Tumor Size, J. Clin. Endoc. Metab,. 87(10), 2002, pp. 4554-4563.
Barradell, L. B. et al., "Histrelin: A Review of its Pharmacological Properties and Therapeutic Role in Central Precocious Puberty," Drugs, vol. 45, No. 4, Apr. 1993, pp. 570-588; published by Adis International Limited.
Chertin et al., "An Implant Releasing the Gonadotropin Hormone-Releasing Hormone Agonist Histrelin Maintains Medical Castration for Up to 30 Months in Metastic Prostate Cancer," Journal of Urology, Baltimore, MD, US, vol. 163. 2000, pp. 838-844.
Chinese Office Action corresponding to CN 2006800160292, dated Sep. 4, 2009, 8 pages.
Eurasian Patent Office Decision on Patentability corresponding to EU 200701956/28, dated Jan. 21, 2009, 6 pages.
New Zealand Patent Office Examination Report corresponding to NZ 561400, dated Jul. 28, 2009, 2 pages.
Feuillan, P. P. et al., "Follow-up of children and young adults after GnRH-agonist therapy for central precocious puberty," J. Endocrinol. Invest., vol. 24, 2001, pp. 734-736; published by Editrice Kurtis.

(56) References Cited

OTHER PUBLICATIONS

International Search Report and Written Opinion, PCT/US2009/050215, dated Nov. 25, 2009, 11 pgs.
International Search Report, PCT/US00/01664, dated Jul. 13, 2000, 1 pg.
International Search Report, PCT/US06/08891, dated Dec. 4, 2006, 2 pgs.
International Search Report, PCT/US2005/021368, dated Oct. 23, 2006, 3 pgs.
International Search Report, PCT/US2008/061511, dated Nov. 8, 2009, 2 pgs.
Lan NaLee, "Volume of Blood in a Human," from http://hypertextbook.com/facts/1998/LanNaLee.shtml, (1998) updated (2001).
Langer, "Implantable Controlled Release Systems," Pharmac. Ther. (1983), vol. 21, p. 35-51.
P. Kuzma et al., U.S. PTO Office Action, U.S. Appl. No. 11/155,822 dated Jan. 22, 2008, 12 pgs.
P. Kuzma et al., U.S. PTO Office Action, U.S. Appl. No. 11/155,822 dated Feb. 18, 2009, 11 pgs.
P. Kuzma et al., U.S. PTO Office Action, U.S. Appl. No. 11/155,822 dated Oct. 13, 2009, 21 pgs.
Schlegel et al., "Effective Long-Term Androgen Suppression in Men with Prostate Cancer Using a Hydrogel Implant with the GnRH Agonist Histrelin," Urology, vol. 58, 2001, pp. 878-582.
Office Action Issued by the Japanese Patent Office for Application No. 2010-506506 dated Jan. 20, 2015.
Office Action Issued by the Korean Intellectual Property Office for Application No. 10-2009-7023460 dated Dec. 28, 2014.
Office Action Issued by the Japanese Patent Office for Application No. 2014-081331, dated May 12, 2015 (English Translation Only).
Office Action Issued by Canadian Intellectual Property Office for Application No. 2,685,397, dated Apr. 13, 2015.

* cited by examiner

IMPLANT DEVICE RELEASE AGENTS AND METHODS OF USING SAME

CROSS-REFERENCE TO RELATED APPLICATION

This application claims the benefit of U.S. Provisional Application 60/914,511 which was filed on Apr. 27, 2007, and which is hereby incorporated by reference, in its entirety, for any and all purposes.

FIELD

In general, the invention is related to medical implant devices and methods of their preparation.

BACKGROUND

Drugs may be delivered to patients by a variety of methods including oral, intravenous administration, inhalation of aerosols, a transdermal patch, and subcutaneous implants. The method chosen depends, among other things, upon the desired therapeutic concentration of the drug or pharmaceutical to be achieved in the patient and the duration the concentration must be maintained.

Subcutaneous implants are introduced under a patient's skin and allow a drug or other pharmaceutical material to be subcutaneously introduced or administered to the patient. In general, a drug administered by a subcutaneous implant is slowly released over a long period of time allowing a uniform dose of the drug to be dispensed over many months or years.

The size and shape of an implant are important in determining the rate of delivery of a particular drug from a subcutaneous implant. Practical considerations put constraints on the dimensions of a subcutaneous implant. For example, the length of a typical implant is generally limited to about 1½ to 2 inches long because longer implants are difficult to accurately position, may be more susceptible to breakage, which can affect drug delivery rate, and in general, are more cumbersome and cosmetically apparent. Because of this, it may be necessary to implant a plurality of individual, shorter implants to provide the desired amount of a drug rather than as a single longer implant. However, administering more than one implant can also be time consuming, cumbersome and cost-prohibitive.

The active agent administered using subcutaneous implants, such as, for example, a drug or pharmaceutical material, may be imbedded in cartridges made of biologically inert polymers. In such cases, cartridges are generally cylindrical hollow tubes made by extrusion, injection molding, reaction injection molding, compression molding, or spin-casting depending on the type of polymer used. Such cylindrical hollow tubes may have one or two open ends. For example, U.S. Pat. Nos. 5,266,325, 5,292,515, and 6,361,797, herein incorporated by reference in their entireties, describe methods for spin casting suitable cartridges. Following molding or casting, the active agent may be introduced into the hollow core, or reservoir of the cartridge, usually in the form of a pellet. Additional liquid material that is polymerizable may be introduced into the core opening and cured to seal the cartridge.

Release agents to aid in removal of a cartridge from a mold are well known in the art. Such release agents are generally dip-coated, sprayed or painted onto or into the mold, and allow molded polymerized material, which may otherwise adhere to the mold, to be easily ejected from the mold. However, residual release agents may adhere to molded articles, and, in the case of an implant device that must be clean and sterile, these release agents must either be removed from the surface of the implant device or be made of a material that can be introduced into a patient without inducing a negative reaction.

The problem of leaving residual release agents, discussed above, can, perhaps, be circumvented by combining a release agent with polymerizable material that will ultimately form the cartridge, prior to introducing the polymerizable material to a mold—provided, of course, that the release agent must be safe for introduction into a patient and must not adversely react with the polymer of the molded article, to cause, for example, weakening of the structure of the article. Accordingly, in one aspect of the invention, effective release agents are provided that do not react undesirably with the polymer of the cartridge and can be safely introduced into a patient. Additionally, selected release agents, as described further below, protect the polymer cartridge from adverse effects of sterilization.

SUMMARY

In a first aspect, a device is provided having a polymeric material and a release agent, in which the device is a molded, reservoir implant, and the release agent has a molecular weight of at least 1000 g/mol. In some embodiments, the release agent is a non-ionic surfactant. For example, the non-ionic surfactant may include, but is not limited to, a polyethylene glycol hydrophilic tail and a lipophilic head. In some embodiments, the release agent is selected from Brij 35, polyoxyetheylene(20)sorbitan trioleate, Tween 20, Tween 80, and/or Vitamin E TPGS, or a mixture of any two or more. In yet other embodiments, the release agent has a molecular weight (MW) of at least about 1200.

In some embodiments, the reservoir implant is a dry implant (that is, not hydrated). The dry implant may be further described as having a surface area of about 350 mm$^2$, or greater, in some embodiments, or from about 350 mm$^2$ to about 600 mm$^2$, in other embodiments.

In yet other embodiments, the reservoir implant is a hydrated implant. The hydrated implant may be further described as having a surface area of about 500 mm$^2$, or greater, in some embodiments, or from about 500 mm$^2$ to about 800 mm$^2$, in other embodiments.

In another aspect, a process is provided for preparing implant devices. Such processes may include charging a polymerization column or a mold with a monomer and a release agent; and rotating the polymerization column or mold about its longitudinal axis at a speed sufficient to displace the monomer radially outward along the interior surfaces of the polymerization column or mold; maintaining the polymerization column or mold at a position substantially parallel to the ground; polymerizing the liquid polymerizable material; and recovering a reservoir implant device, including at least a portion of the release agent, in which the release agent has a molecular weight (MW) of at least 1000.

DETAILED DESCRIPTION

Before the present compositions and methods are described, it is to be understood that this invention is not limited to the particular molecules, compositions, methodologies or protocols described, as one of ordinary skill in the art will recognize that these examples may vary. It is also to be understood that the terminology used in the description is for the purpose of describing the particular versions or embodiments only, and is not intended to limit the scope of the present invention, which is limited only by the appended claims. The terms used herein have meanings recognized and known to those of skill in the art; however, for convenience and completeness, selected terms and their meanings are set forth below.

It must also be noted that as used herein and in the appended claims, the singular forms "a", "an", and "the" are intended to include plural references unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference to the extent they support the present invention. Nothing herein is to be construed as an admission that the invention is not entitled to antedate such disclosure by virtue of prior invention.

As used herein, the term "about" means plus or minus 10% of the numerical value of the number with which it is being used. For example, about 50% means in the range of 45%-55%.

"Controlled release formulation" refers to a formulation designed to consistently release a predetermined, therapeutically effective amount of drug or other active agent such as a polypeptide or a synthetic compound over an extended period of time, with the result being a reduction in the number of treatments necessary to achieve the desired therapeutic effect. A controlled formulation would aid in decreasing the number of treatments necessary to achieve the desired effect. Controlled release formulations may achieve a desired pharmacokinetic profile in a subject, through commencement of the release of the active agent substantially immediately after placement in a delivery environment, followed by consistent, sustained, release of the active agent. In some embodiments, the release of the active agent is zero-order or near zero-order.

The terms "patient" and "subject" mean all animals including humans. Examples of patients or subjects include humans, cows, dogs, cats, goats, sheep, and pigs.

The term "pharmaceutically acceptable salts, esters, amides, and prodrugs," as used herein, refers to those carboxylate salts, amino acid addition salts, esters, amides, and prodrugs of the compounds which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds.

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

In addition, the compounds can exist in unsolvated as well as solvated forms with pharmaceutically acceptable solvents such as water, ethanol, and the like. In general, the solvated forms are considered equivalent to the unsolvated forms.

The expression "macromolecular drug," as used herein, is intended to include drugs, i.e., a substance that affects the activity of a specific bodily organ or function, having a molecular weight of greater than 1,000 g/mol, in some embodiments, from about 1,000 g/mol to about 25,000 g/mol, in other embodiments, or greater than 25,000 g/mol in yet other embodiments. Some drugs, e.g., steroids, anabolic agents and insulin, are characterized by a tendency toward aggregation with a resulting decrease in solubility. Suitable drugs include but are not limited to endocrine agents, chemotherapeutic agents, antibiotics, anti-drug addiction agents, oncological treating agents, anti-fungal agents, anti-pulmonary dysfunction agents, enzymes and macromolecular proteins affecting the central nervous system. Preferred macromolecular drugs include native and recombinant bioactive proteins and analogs thereof, such as (1) growth hormones and analogs thereof, (2) insulin and insulin-like growth factors such as somatomedins and analogs thereof, and (3) other pituitary derived hormones such as prolactin and analogs thereof.

The term "salts" refers to the relatively non-toxic, inorganic and organic acid addition salts of compounds provided herein. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetraethylammonium, methylamine, dimethylamine, trimethylamine, triethylamine, ethylamine, and the like. (See, for example, S. M. Barge et al., "Pharmaceutical Salts," J. Pharm. Sci., 1977, 66:1-19 which is incorporated herein by reference.).

"Treatment" refers to the administration of medicine or the performance of medical procedures with respect to a patient, for either prophylaxis (prevention) or to cure the infirmity or malady in the instance where the patient is afflicted.

A "therapeutically effective amount" is an amount sufficient to decrease, prevent, or ameliorate the symptoms associated with a medical condition. In the context of hormonal therapy it can also mean to normalize body functions or hormone levels in disease or disorders.

Unless the context indicates otherwise, the term "copolymer" includes polymers made by polymerizing a mixture of at least two ethylenically unsaturated monomers.

By the term "HEMA unit(s)" is meant the structure

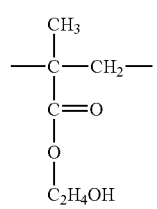

recurring in the polymer obtained by polymerizing hydrophilic material containing 2-hydroxyethyl methacrylate ("HEMA").

By the term "HPMA unit(s)" is meant the structure

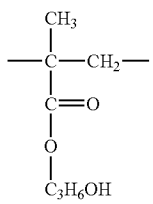

obtained by polymerizing hydrophilic material containing hydroxypropyl methacrylate ("HPMA").

By the term "HBMA unit(s)" is meant the structure

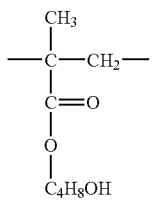

recurring in the polymer obtained by polymerizing hydrophilic material containing 2-hydroxybutyl methacrylate ("HBMA").

Embodiments described herein are generally directed to release agents used in the production of molded articles for use as medical devices. In general release agents are compounds capable of allowing effective release of a molded article from a mold. However, release agents for use in medical devices may also be non-reactive to the molded article, can be safely introduced into a patient, and in certain embodiments, may guard against adverse effects on the molded article caused by the sterilization process.

The release agents, embodied herein, are generally non-ionic surfactants, and in a preferred embodiment, the release agent is Vitamin E TPGS. Vitamin E TPGS is an abbreviation for D-α-tocopheryl (Vitamin E) polyethylene glycol 1000 succinate. These release agents provide excellent release properties and are non-reactive to the molded article while providing a safety profile that is suitable for implants. Additionally, these release agents can act as antioxidants or free radical scavengers and, therefore, prevent or reduce adverse effects on the molded article associated with sterilization of the molded article, especially sterilization methods that can generate free radicals, including irradiation methods. In particular embodiments, the release agent dissolves in a desired monomer mixture. For example, a hydrophilic monomer material, such as, for example combinations of HEMA, HPMA and HBMA, may be used in combination with an amphiphilic release agent, such as, Vitamin E TPGS, during the molding process.

Non-ionic surfactants are known in the art, and may generally consist of a polyethylene glycol hydrophilic tail and a lipophilic head. For example, in Vitamin E TPGS, the lipophilic head is tocopherol succinate and for Triton X-100 it is an isooctylphenyl group. Non-ionic surfactants may be characterized by several parameters, such as, for example, hydrophilic-lipophilic balance (HLB), which relates the size of the polyethylene glycol tail to the lipophilic head; critical micelle concentration (CMC), which is the concentration of surfactant at which micelles form; and molecular weight (MW), which shows the size of the hydrophilic and lipophilic portions relative to other surfactants with similar properties. Additionally, CMC is an indication of the surface activity of the surfactant, and a low CMC is indicative of a more stable micelle because of stronger binding forces. Table 1 below lists several surfactants and their physical properties.

TABLE 1

| Surfactants | | | |
|---|---|---|---|
| Name | ~MW | HLB | CMC (mM) |
| Triton X-100 | 625 | 13.5 | 0.2-0.9 |
| Vitamin E TPGS | 1513 | 13 | 0.1 |
| Triton X-114 | 537 | 12.4 | 0.2 |
| Brij 35 | 1200 | 16.9 | 0.05-0.1 |
| Tween 20 | 1228 | 16.7 | 0.06 |
| Tween 80 | 1310 | 15 | 0.012 |
| Sucrose monolaurate | 525 | ~8 | 0.2 |

Additional release agents for use in combination with implant devices may include, but are not limited to, polyoxyethylene(2) stearyl ether, sorbitan monolaurate, polyoxyethylene(5)nonylphenyl ether, polyoxyetheylene(20)sorbitan trioleate, polyoxyethylene(10)isooctylphenyl ether, and the like, or combinations of these release agents.

In certain embodiments, the release agent is a polyoxyethylene ester of fatty acids or other hydrophobic compounds. These compounds are well known in the art and include a polyoxyethylene tail and a saturated or unsaturated hydrophobic head. The hydrophobic moiety of various embodiments may include any aromatic group containing moiety or polycyclic aromatic moieties such as, for example, a phenol, a catechol, a resorcinol, a hydroquinone, a tocopherol, Vitamin E, and the like and may be isoprenoid or non-isoprenoid. The side chains associated with these aromatic moieties may be of any length and may additionally include any number of double bonds and/or substitutions. For example, non-ionic surfactants may include, but are not limited to, naturally occurring or commercially manufactured tocopherols including any isoform, racemate, or chemically modified derivative, such as, Vitamin E TPGS. Tocopherols may also include oxidation products of tocopherols, such as the oxidation products of α-tocopherol, tocopherol quinones, tocopherol hydroquinones, epoxytocopherols, and nitrotocopherols.

Without being bound by theory, it is believed that higher molecular weight release agents provide improved release characteristics than lower molecular weight release agents. As such, in preferred embodiments, the release agents have a molecular weight (MW) in excess of about 1000. In other embodiments, the release agents have a molecular weight (MW) in excess of about 1200. In yet other embodiments, the release agents have a molecular weight (MW) from about 1000 to about 2000, preferably between about 1200 and about 1800.

The molded articles of embodiments may be any molded article, and in particular, the molded article may be used in a medical device such as an implant device for drug delivery. Drug delivery implant devices are highly useful in the delayed/sustained and the immediate/sustained release of active agents to animals, e.g., humans, sheep, dogs, cats, turkeys, cattle, and the like. Such implant devices are known in the art and are described in, for example, U.S. Pat. Nos. 5,266,325; 5,292,515; and 6,361,797, incorporated herein by reference in their entireties.

In various embodiments, a cartridge used as an implantable drug delivery device may be molded into any shape, including, but not limited to a cylinder or a ring shape, and the dimensions of the cartridge can vary depending on the application. In particular embodiments, the drug delivery devices prepared using the release agents are cylindrically shaped implants containing within the internal reservoir or "core" an active agent, and optionally, a pharmaceutically acceptable carrier. The membrane thickness (between the interior and exterior surfaces) of the implant may be substantially uniform, and may serve as a rate-limiting barrier for the release of the contained agent. Such implants can be plasticized or hydrated and reshaped into other geometrically shaped articles for use in various medical applications. The hydrophilic implant as a xerogel readily absorbs water, and in a hydrated state it is referred to as a hydrogel. In either form, it is biocompatible, non-toxic to the host, non-biodegradable and, water-swellable and water-insoluble.

Suitable delivery devices may be capable of delayed/sustained release of therapeutic dosages of an active agent into an aqueous delivery environment. As used herein, the term "active agent" or "active compound" broadly includes any compound or mixture of compounds that are capable of being delivered from the implantable delivery device to produce a beneficial and useful result. The active agents whether in solid or liquid form may have sufficient solubility or miscibility in an aqueous system to render them capable of being released through the tailor-made hydrogel membranes into the delivery environment. The term "drug" including "macromolecular drug," as used herein, may include any physiologically or pharmacologically active substance that produces a localized or a systemic effect in a subject. The active agents may include inorganic and organic drugs that act on the central nervous system, psychic energizers, tranquilizers, anti-convulsants, muscle relaxants, anti-parkinson, analgesic, anti-inflammatory, anesthetic, anti-spasmodic, muscle contractants, anti-microbials, anti-malarials, hormonal agents, sympathomimetic, cardiovascular, diuretics, anti-parasitic and the like.

In various embodiments, the drug delivery device may contain an active agent and a pharmaceutically acceptable carrier which may be in any form such as, but not limited to, suspending media, solvents, aqueous systems, solid substrates or matrices and the like. Suspending media and solvents may include, for example, oils such as silicone oil (particularly medical grade), corn oil, castor oil, peanut oil and sesame oil; condensation products of castor oil and ethylene oxide combining about 30 to 35 moles of ethylene oxide per mole of castor oil; liquid glyceryl triesters of a lower molecular weight fatty acid; lower alkanols; glycols; polyalkylene glycols. An aqueous system may include, for example, sterile water, saline, dextrose, dextrose in water or saline, and the like. Solid substrates or matrices may include, for example, starch, gelatin, sugars (e.g., glucose), natural gums (e.g., acacia, sodium alginate, carboxymethyl cellulose), and the like. In addition, the carrier may also contain adjuvants such as preserving, stabilizing, wetting and emulsifying agents, and the like.

The physical dimensions of the implant device may be determined based on the total amount of active agent to be delivered, the desired daily dosage, and the duration of delivery. For example, a larger implant may be required to provide sufficient surface area for the release of a higher daily dose of a given active agent. In contrast if the active agent is to be released at a lower daily dosage a smaller implant may be used. Similarly, the thickness of the walls of the cartridge may be increased or the number or size of pores in the cartridge may be decreased or a polymer that allows slower diffusion of the active agent through the cartridge wall may be used to provide a lower dosage over a longer period of time. It should be understood that this time factor is a variable depending on the rate-releasing membrane of choice, its interconnecting pore structure, the active compound, the solubility of the active compound in the liquid medium, and other considerations well known to those skilled in the art. In general, the duration of delivery may range from several days to a few years, preferably, about 1 week to 18 months, and longer.

The volume of the cylindrical reservoir or "core" of a cylindrically-shaped cartridge of the implant device is equal to $\pi r_i^2 h$ wherein $r_i$ is the radius of the reservoir and h is its height. The formula for steady state release from a cylinder is:

$$[dQ/dt] = [2\pi h DK_d C_d]/[\ln(r_o/r_i)]$$

wherein dQ/dt is the rate of diffusion for the active agent through the polymeric material (µg/hr); and $r_o$ is the outside radius of the cylindrical device. Therefore, the thickness of the membrane is, therefore, $r_o - r_i$. $DK_d$ is the membranes permeability coefficient ($cm^2$/hr) wherein D is the diffusivity of the membrane ($cm^2$/hr) and $K_d$ is the partition coefficient for the membrane/carrier. $C_d$ is the concentration of active agent in the carrier (µg/$cm^3$). Steady state release is obtained when $C_d$ is maintained at saturation. Using the determined steady state release constant, the daily dosage, the duration of delivery, and the volume of the active agent and carrier formulation, the volume of the core can be readily determined, and a mold may be prepared to create a cartridge of the appropriate size.

In certain embodiments in which a cylindrical cartridge is used as a drug delivery device that is implanted subcutaneously in a subject, such as, a human or other animal, the length of the hydrated cartridge may be from about 5 mm to about 60 mm, and the external diameter may be from about 1.5 mm to about 5 mm. While the release agents may be used in any size implant, in some embodiments, the release agents are used in the preparation of larger implant devices. For example, the length of a hydrated cartridge prepared using a non-ionic surfactant release agent may be from about 40 to about 60 mm, and the external diameter may be from about 3 to about 5 mm. In some embodiments, the length of a hydrated cartridge is 45 to 60 mm, and the external diameter is from 3.5 to 4.8 mm. Without wishing to be bound by theory, non-ionic surfactant release agents may overcome the surface tension in molds used during preparation of cartridges while allowing the cartridge to be readily released from the mold. In certain embodiments, a larger cartridge may be used for large animals or livestock, such as, for example, sheep, cows, goats, cattle, and the like because larger animals can tolerate implantation of larger drug delivery devices.

In certain other embodiments where a cylindrical cartridge is used as a drug delivery device the size of the cartridge may be described in terms of the external surface area of the device. That said, hydrated implants and xerogel (i.e., non-hydrated, or dry) implants have different dimensions and therefore different surface areas. As noted above, in some embodiments, the release agents are used in the preparation of larger implant devices. For example, a xerogel, non-hydrated, or dry implant may have a surface area of about 350 $mm^2$, or greater. Alternatively, a xerogel, non-hydrated, or dry implant may have a surface area of from about 350 $mm^2$ to about 600 $mm^2$. For example, the dry implant may have a surface area from 378 $mm^2$ to 660 $mm^2$. Additionally, a hydrated implant may have a surface area of about 500 $mm^2$, or greater. Or, alternatively, the hydrated implant may have a surface area of from about 600 $mm^2$ to about 800 $mm^2$. As used herein, the term "hydrated implant" refers to implants having a water content of 5 wt %, or greater, and are thus soft and flexible. As used herein, dry implant refers to implants, which are rigid and inflexible, having a water content less than 5 wt %, in some embodiments, and less than 1 wt %, in some other embodiments.

Any polymerizable material may be used to prepare various parts of the implants, and in certain embodiments, polymerizable hydrophilic, ethylenically unsaturated compounds may be used to make the cartridges. Examples of hydrophilic monomers that may be used in various embodiments include, but are not limited to, monoesters of an acrylic acid or methacrylic acid with a polyhydroxy compound having an esterifiable hydroxyl group and at least one additional hydroxyl group such as the monoalkylene and polyalkylene polyols of methacrylic acid and acrylic acid, such as, for example, 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, such as, methyl substituted N-vinylpyrrolidone; N-vinylcaprolactam; the alkyl-substituted N-vinylcaprolactam, such as, for example, N-vinyl-2-methylcaprolactam, N-vinyl-3,5-dimethylcaprolactam, and the like.

In various embodiments, the polymerizable material may further include one or more polymerizable hydrophobic monomers. Polymerizable hydrophobic co-monomers are substantially water-insoluble compounds lacking hydrophilic groups or other groups that would decrease the equilibrium water content value of the resulting hydrophilic heterogeneous polymer and it has been shown that increasing the concentration of hydrophobic monomers resulted in heterogeneous hydrophilic polymers having decreasing equilibrium water content. Therefore, in some embodiments, a certain amount of polymerizable hydrophobic monomer may be added to a polymerizable hydrophilic material to vary the equilibrium water content value of the water-swellable polymeric cartridge. Examples of polymerizable hydrophobic comonomers may include; alkyl 2-alkenoates, alkoxyalkyl 2-alkenoates, and the vinyl esters, such as, but not limited to, alkyl acrylate, alkyl methacrylate, alkoxyalkyl methacrylate, alkoxyalkyl acrylate, poly(alkoxy)alkyl methacrylate, vinyl alkanoate, and the like, including, but not limited to, methyl acrylate, methyl methacrylate, ethyl acrylate, ethyl methacrylate, propyl methacrylate, butyl acrylate, butyl methacrylate, methoxymethyl acrylate and methacrylate, ethoxymethyl acrylate and methacrylate and methoxyethyl methacrylate, vinyl acetate, and vinyl propionate. However, it should be understood that these polymers may contain non-homogeneous alternating hydrophobic and hydrophilic polar regions, and non-polar crosslinking agents, such as, for example, EGDMA, may concentrate in the non-polar hydrophobic regions of the polymer during polymerization causing a crosslinking density gradient in the polymer. Such polymers are characterized by over-crosslinking in the hydrophobic segments and by under-crosslinking in the hydrophilic segments which can make the final molded article weak and fragile.

Therefore, in some embodiments, the polymerizable material may include at least two polymerizable hydrophilic monomers. For example, mixtures such as 2-hydroxyethyl methacrylate and hydroxypropyl methacrylate or 2-hydroxyethyl methacrylate and N-methylacrylamide may be used. In such embodiments, the equilibrium water content can be adjusted by varying amounts of two hydrophilic monomers. Without wishing to be bound by theory, molded articles prepared from a homogeneous hydrophilic polymer may be more uniformly cross-linked than articles prepared from heterogeneous polymer mixtures and may not be as weak or fragile. In particular embodiments, cartridges may be prepared from a liquid hydrophilic monomer like HEMA to form polyHEMA. PolyHEMA is a homogeneous, hydrophilic homopolymer having an interfacial free energy close to zero that is strongly biocompatible with body tissue. Mixtures of HEMA including varying quantities of one or more other polymerizable hydrophilic co-monomers can be polymerized to give predictable homogeneous hydrophilic copolymers having useful properties.

In one embodiment, a pore-forming material can be included with the polymerizable hydrophilic material. Pore-formers may be liquid or solid and organic or inorganic and range in size from less than 0.1 micron to several microns depending on the porosity desired in the hydrophilic polymer. In general, pore-formers may be uniformly distributed or dispersed in the liquid polymerizable material and extracted from the resulting molded hydrophilic cartridge without altering the chemical structure of the polymerized hydrophilic polymer. Examples of pore-formers include, but are not limited to, sodium chloride, potassium phosphate, calcium nitrate, mono- and polysaccharides, and the like.

Any crosslinking agent known in the art may be used in the polymerizable material to initiate and/or maintain crosslinking of the polymerizable material, and include, but are not limited to, polyethylenically unsaturated compounds having at least two polymerizable ethylenic sites, such as, for example, di-, tri- and tetra-ethylenically unsaturated compounds, for example, tri-unsaturated crosslinking agents with/without the diunsaturated crosslinking compounds, such as, divinylbenzene, ethylene glycol dimethacrylate and diacrylate, propylene glycol dimethacrylate and diacrylate; and di-, tri- and tetra-acrylate or methacrylate esters of polyols including: triethanolamine, glycerol, pentaerythritol, 1,1,1-trimethylolpropane; trimethylolpropane trimethacrylate (TMPTMA), and the like.

In various embodiments, polymerization of polymerizable materials may be catalyzed or initiated with, for example, free-radical generating compounds, such as, organic peroxides, percarbonates, hydrogen peroxides, and alkali metal sulfates. Further examples of polymerization catalysts and initiators include, but are not limited to, cumene hydroperoxide, t-butyl hydroperoxide, benzoyl peroxide, bis(4-t-butylcyclohexyl)peroxydicarbonate, hydrogen peroxide, 2,4-dichlorobenzoyl peroxide, acetyl peroxide, di-n-propyl peroxydicarbonate, di-tert-butyl peroxide, di-sec-butyl peroxydicarbonate, ammonium sulfate, potassium sulfate, and sodium sulfate. In particular embodiments, a catalyst may be effective at moderately low temperature such as at about 20° C. to about 80° C., such as, for example, tert-butyl peroctoate, benzoyl peroxide, and di(secbutyl)peroxydicarbonate.

In another embodiment, a conventional redox polymerization catalyst may be employed. Without wishing to be bound by theory, initiation of polymerization using a redox catalyst may be advantageous because polymerization may occur at reasonable rates at low temperatures, such as, for example, about 0° C. to about 50° C. Any redox polymerization catalyst known and used in the art may be used in polymerization reactions, such as, sodium bisulfate, ammonium persulfate, sodium thiosulfate and potassium persulfate, and the like.

The polymerizable material may be prepared by any method. For example, in one embodiment, the polymerizable monomers may be combined with a release agent in a single mixture. Optional a pore-former, a crosslinking agent, and/or a polymerization initiator may also be added. In another embodiment, the polymerizable monomers, and crosslinking agent may be combined to form a master batch, and a pore-former, a polymerization initiator, and a release agent may be added to the master batch or a portion of the master batch prior to polymerization. In yet another embodiment, additional release agent may be used to coat interior surfaces of the mold. In such embodiments, the same release agent incorporated into the liquid polymerizable material or a different release agent may be applied to the mold or polymerization column by any method known in the art, such as, for example, dip-coating, spraying or painting onto interior surfaces of the mold. In general, enough release agent may be used to completely cover all of the interior surfaces of the mold with a thin layer of the release agent.

Polymerization of the polymerizable material may be carried out in bulk or with an inert solvent. In embodiments in which a solvent is used, suitable solvents may include water; organic solvents such as water-soluble lower aliphatic monohydric alcohols as well as polyhydric alcohols, such as, for example, glycol, glycerine, dioxane, and the like, and mixtures of solvents.

In certain embodiments, polymerization of the polymerizable material may be effected using electromagnetic radiation, such as, for example, U.V., X-Ray, gamma, or microwave radiation as well as any other form of radiation known in the art. In general, a catalytically effective amount of a catalyst and/or initiators and/or electromagnetic radiation may be employed to optimize the polymerization reaction. For example, in a particular embodiment, the liquid polymerizable material including the catalyst benzoin methyl ether (BME) is cured using U.V. radiation.

Cartridges may be prepared from any of the materials described herein above using any method known in the art, such as, for example, extrusion, injection molding, reaction injection molding, compression molding, or spin-casting. In an exemplary embodiment, an implant device is made by centrifugally-casting or spin-casting wherein a cartridge is prepared by preparing a polymerization column or mold of appropriate size with one extremity of the column being closed and the other extremity being open-ended and adapting the polymerization column or mold for rotation about its longitudinal axis; introducing a monomer to the column or mold; rotating the column or mold about its longitudinal axis and maintaining it substantially parallel to the ground at a speed sufficient to displace the monomer radially outward along the interior surfaces of the column or mold such that the monomer assumes a cylindrical configuration with a core; polymerizing the monomer to convert it to a solid molded article having a concentric cylindrical core; and recovering the article, or reservoir cartridge.

In general, molds or polymerization columns as described herein have interior surfaces that are cylindrical, such that cross-sectional areas of the interior of the column are circular in shape and about equal in diameter and smooth. Molds or polymerization columns of various embodiments can be made of any suitable material such as, for example, plastics, including, but not limited to, polyethylene, polypropylene, and polystyrene; metal; glass; and the like. In some embodiments, the column may be fabricated from a material that allows electromagnetic radiation to pass into the polymerization zone of the column, and in certain embodiments, glass, such as Pyrex™, is used to make the mold or polymerization column.

The monomer(s), or polymerizable material as prepared above may then be introduced to the mold. The mold or polymerization column may then be rotated about its longitudinal axis and maintained in a position parallel to the ground until the polymerizable material has stabilized to the predetermined shape. The speed at which the mold or polymerization column is rotated may vary, depending upon the size of the cartridge being made, the type of polymerizable material being used, and the effectiveness of the release agent. For example in some embodiments, the rotational speed may be from less than about 1000 rpm to greater than 6000 rpm, and in certain embodiments, the rotational speed may be about 2150 rpm.

Having obtained the predetermined shape, the polymerizable material may be polymerized and cured. Curing may occur using numerous methods and for any period of time depending on the type of polymerizable material used and the size of the cartridge being prepared. For example, when the polymerizable material has achieved the predetermined shape, the mold or polymerization column may be irradiated with U.V. light for a period of time, such as, for example, from about 1 to about 10 minutes, to initiate polymerization of the polymerizable material. The cartridge may then undergo thermal curing and annealing. For example, the cartridge may be thermally cured for about 60 minutes at a temperature up to about 100° C. followed by post-curing for about 30 minutes at a temperature up to about 120° C. and annealing for about 30 minutes at about up to 130° C. with gradual cooling to ambient temperature (about 25° C.). The cured cartridge may be removed from the mold or polymerization column, washed to remove excess release agent and/or to extract pore-formers, and polished to achieve a smooth, unscored surface.

In some embodiments, the cartridges are used in the fabrication of the drug delivery device. In such embodiments, a predetermined amount of an active agent, such as a drug; or an admixture or suspension of an active agent and an inert, non-toxic material, such as medical grade silicone oil; may be introduced into the cartridge, partially filling the core. In some embodiments, a layer of an inert material, such as, Teflon tape, may be placed on top of the active agent, and the void in the core above the covering may be sealed to prevent leakage into or out of the cartridge. The seal may be formed by filling the void with a polymerizable material, such as a polymerizable material used to make the cartridge, and polymerizing the polymerizable material to form a plug that seals the opening of the cartridge. In some embodiments, the polymerizable material used to form the plug may be the liquid polymerizable material used to make the cartridge and may not have an equilibrium water content value exceeding the equilibrium water content value of the hydrophilic cartridge, upon maximum hydration. In other embodiments, the polymerizable material may be of similar composition but with a higher hydrophilicity than the liquid polymerizable material employed in the fabrication of the cartridge.

In one exemplary embodiment, a plug for a cartridge having a core filled with an active agent covered with teflon tape, may be made by first cleaning and slightly increasing the internal surface area of the core above the agent by careful reaming the open end of the cartridge with an appropriate reamer. The reamed surface area may then be cleaned with a sufficient amount of a mono- or polyhydric alcohol, such as, for example, ethanol, causing a slight swelling of the surface of the cartridge. Using a fine needle-syringe, a small amount of the liquid polymerizable material may be injected into the cartridge filling the core to the top. The polymerizable material may then be polymerized by positioning the cartridge so that its longitudinal axis is perpendicular to the ground, rotating the cartridge on using for example, a lathe at a relatively low speed, such as, about 100 rpm to about 200 rpm, and exposing the cartridge to U.V. light for several minutes, for example, 5-10 minutes. In the event the active agent is sensitive to U.V. light, a shield such as, for example, aluminum foil may be used to shield the active compound from the U.V. light. In general, the curing of the plug should take place at a temperature that is not detrimental to the drug, for example, ambient temperature. Without wishing to be bound by theory, reaming and cleaning the open end of the cartridge promotes the penetration of the polymerizable hydrophilic material into the treated surface.

The filled and sealed cartridges may be sterilized by any sterilization technique known in the art, depending on the material used to make the cartridge and the active agent to be delivered. For example, suitable sterilization techniques may include, but not be limited to, heat sterilization, radiation sterilization, such as cobalt 60 irradiation, gamma radiation, or electron beams, ethylene oxide sterilization, and the like. In certain embodiments, agents affixed to the cartridge may act as an antioxidant or free radical scavenger during sterilization to reduce or eliminate the adverse affects of free radicals formed during sterilization by, for example, irradiation.

In various embodiments, the cartridges and/or medical devices described above may be stored prior to or following sterilization, and the cartridges may be stored in either wet or dry packaging. In embodiments in which the cartridge is stored in wet packaging, the packaging may include a hydrating liquid. The hydrating liquid may simulate the environment in which the active compound will be released; for example, the hydrating liquid may mimic body fluid, sterile water, tear fluid, physiological saline solution, phosphate buffer solution, and the like. In embodiments in which the cartridge is stored in dry packaging, the cartridge may be incubated in any of the hydrating liquids described above prior to use. For example, a dry cartridge used as an implant device may be hydrated in sterile physiological saline solution prior to implantation. Alternatively, some implants may self-hydrate upon implantation as a dry implant, and thus, no hydration of the implant prior to implantation is necessary.

One skilled in the art will readily realize that all ranges and ratios discussed can and do necessarily also describe all subranges and subratios therein for all purposes and that all such subranges and subratios also form part and parcel of this invention. Any listed range or ratio can be easily recognized as sufficiently describing and enabling the same range or ratio being broken down into at least equal halves, thirds, quarters, fifths, tenths, etc. As a non-limiting example, each range or ratio discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLE 1

Table 2 describes some monomer mixtures that were prepared.

TABLE 2

Monomer Mixtures

| Implant | % HEMA | % HPMA | % TMPTMA | % BME | % P-16 | % Triton X-100 | % Vitamin E TPGS |
|---|---|---|---|---|---|---|---|
| 1 | 40 | 59.5 | 0.5 | 0.3 | 0.1 | 1.0 | |
| 2 | 40 | 59.5 | 0.5 | 0.3 | 0.1 | | 1.0 |

Spin-casting and polymer release characteristics were to be evaluated and tabulated at time intervals of zero weeks, one week, two weeks, and four weeks, designated as $T_0$, $T_{1\ week}$, $T_{2\ weeks}$, $T_{3\ weeks}$, and $T_{4\ weeks}$, respectively, on three consecutive days, using 20 glass molds treated with 1% polydimethylsiloxane each day.

For implant 1, the first cycle of the first time point did not give acceptable release characteristics and the experiment was abandoned. As used herein, the phrase "acceptable release characteristics" indicates that the implant, once polymerized in the mold, is capable of being removed from the mold without impacting the integrity of the implant. For example, the implant having a release agent will release from the mold without disrupting the implant by tearing, breaking, cracking, or other deleterious events. As a result of the unacceptable release characteristics of Implant 1, without being bound by theory, it is believed that one factor for acceptable release characteristics may be the molecular weight of the release agent.

For implant 2 at each time-point, each set of 20 molds was evaluated for three spin-casting cycles, and, with one exception, on three consecutive days (at $T_0$, the second and third cycles were interrupted by a weekend). For every time-point, no failures were observed by the third cycle, each providing acceptable release characteristics. In 299 total individual spin-casting cycles over a four-week period, not a single failure was observed—the monomer mixture distributed in all molds within an acceptable time frame, and the resulting cartridges were readily removable from the molds following post-cure.

EXAMPLE 2

Monomer mixtures were prepared as follows in Table 3 and below.

TABLE 3

Monomer Mixtures

| Form. | % HEMA | % HPMA | % TMPTMA | % BME | % P-16 | % Antioxidant or Triton (Form. 2-8 do not contain Triton) |
|---|---|---|---|---|---|---|
| 1 | 20 | 79.5 | 0.5 | 0.3 | 0.1 | 1.0% Triton |
| 2 | 20 | 79.5 | 0.5 | 0.3 | 0.1 | 0.1% BHT, 0.1% propyl gallate |
| 3 | 20 | 79.5 | 0.5 | 0.3 | 0.1 | None |
| 4 | 20 | 79.5 | 0.5 | 0.3 | 0.1 | 0.1% BHT |
| 5 | 20 | 79.5 | 0.5 | 0.3 | 0.1 | 0.1% propyl gallate |
| 6 | 20 | 79.5 | 0.5 | 0.3 | 0.1 | 0.05% ascorbic acid, 0.1% propyl gallate |
| 7 | 20 | 79.5 | 0.5 | 0.3 | 0.1 | 0.1% ascorbic acid |
| 8 | 20 | 79.5 | 0.5 | 0.3 | 0.1 | 0.1% Vitamin E TPGS |

Approximately 15-20 cartridges of each formulation were prepared and gamma irradiated at 10-11 kGy. The tensile strength of five cartridges from each formulation was measured initially. The remaining cartridges were stored at 37° C. and tested for tensile strength again at 3 and 8 months. Data are provided in Table 4. Cartridges prepared with Vitamin E TPGS had the highest tensile strength initially after irradiation and after 3 and 8 months storage at 37° C. Ascorbic acid seems to be effective as well, however due to the higher MW of Vitamin E TPGS its effects may last longer than the lower MW antioxidants.

TABLE 4

Tensile Strengths

| Form. | Initial | 3 months | 8 months |
|---|---|---|---|
| 1 | 1.84 | 1.68 | 1.12 |
| 2 | 1.63 | 2.10 | 1.29 |
| 3 | 1.77 | 1.93 | 1.50 |
| 4 | 1.76 | 2.11 | 1.66 |
| 5 | 1.44 | 2.10 | 1.75 |
| 6 | 1.80 | 2.19 | 1.78 |
| 7 | 1.67 | 2.26 | 1.81 |
| 8 | 1.94 | 2.26 | 1.86 |

EXAMPLE 3

Monomer mixtures as described in Example 1 were prepared by loading cartridges of implant 2 with pellets having a composition of 88% octreotide, 10% hydroxypropyl cellulose and 2% magnesium stearate. The total pellet loading was approximately 95-100 mg. Octreotide elution from the implants indicate that Vitamin E TPGS is an acceptable mold release agent and are reported in Table 5.

TABLE 5

Release of Octreotide from Cartridges (µg/day)

| Form. | Day 14 | Day 28 | Day 42 | Day 56 |
|---|---|---|---|---|
| 2 | 261 | 601 | 549 | 468 |

While some embodiments have been illustrated and described, it should be understood that changes and modifications can be made therein in accordance with ordinary skill in the art without departing from the invention in its broader aspects as defined in the following claims.

What is claimed is:

1. A device suitable for implantation into a subject for delivery of an active agent to the subject at a zero-order or near-zero order rate comprising:
    a polymeric material comprising a polymer formed from one or more hydrophilic, ethylenically unsaturated monomers and a release agent;
    wherein the device is a molded, reservoir implant comprising a hollow core for containing the active agent and an optional pharmaceutical carrier; and
    the release agent comprises d-α-tocopheryl polyethylene glycol 1000 succinate (Vitamin E TPGS).

2. The device of claim 1, wherein the reservoir implant is a dry implant.

3. The device of claim 2, wherein the dry implant has a surface area of about 350 mm$^2$ or greater.

4. The device of claim 2, wherein the dry implant has a surface area of from about 350 mm$^2$ to about 600 mm$^2$.

5. The device of claim 1, wherein the reservoir implant is a hydrated implant.

6. The device of claim 5, wherein the hydrated implant has a surface area of about 500 mm$^2$ or greater.

7. The device of claim 5, wherein the hydrated implant has a surface area of from about 500 mm$^2$ to about 800 mm$^2$.

8. The device of claim 1, wherein the polymeric material is prepared from a monomer mixture comprising two or more polymerizable monomers.

9. The device of claim 8, wherein the monomers are selected from 2-hydroxyethyl methacrylate, 2-hydroxyethyl acrylate, hydroxypropyl methacrylate, hydroxypropyl acrylate, hydroxybutyl methacrylate, hydroxybutyl acrylate, diethylene glycol methacrylate, diethylene glycol acrylate, propylene glycol methacrylate, propylene glycol acrylate, dipropylene glycol methacrylate, dipropylene glycol acrylate, glycidyl methacrylate, glycidyl acrylate, glyceryl methacrylate, glyceryl acrylate, N-methylmethacrylamide, N,N-dimethylmethacrylamide, N-vinylpyrrolidone N-vinylmethylpyrrolidone, N-vinylcaprolactam, N-vinyl-2-methylcaprolactam, N-vinyl-3,5-dimethylcaprolactam, or a mixture of any two or more thereof.

10. The device of claim 8, wherein the monomers are selected from methyl acrylate, methyl methacrylate, ethyl acrylate, ethyl methacrylate, propyl methacrylate, butyl acrylate, butyl methacrylate, methoxymethyl acrylate, methoxymethyl methacrylate, ethoxymethyl acrylate, ethoxymethyl methacrylate, methoxyethyl methacrylate, vinyl acetate, vinyl propionate, or a mixture of any two or more thereof.

11. The device of claim 8, wherein the polymerizable monomers are liquids.

12. A process comprising:
charging a polymerization column or a mold with a liquid comprising one or more hydrophilic, ethylenically unsaturated monomers and a release agent;
rotating the polymerization column or mold about its longitudinal axis at a speed sufficient to displace the monomer radially outward along the interior surfaces of the polymerization column or mold;
maintaining the polymerization column or mold at a position substantially parallel to the ground;
polymerizing the liquid polymerizable material; and
recovering a reservoir implant device;
wherein the release agent is Vitamin E TPGS.

13. The process of claim 12, wherein the reservoir implant is a dry implant.

14. The process of claim 13, wherein the dry implant has a surface area of about 350 mm$^2$ or greater.

15. The process of claim 13, wherein the dry implant has a surface area of from about 350 mm$^2$ to about 600 mm$^2$.

16. The process of claim 12, wherein the reservoir implant is a hydrated implant.

17. The process of claim 16, wherein the hydrated implant has a surface area of about 500 mm$^2$ or greater.

18. The process of claim 16, wherein the hydrated implant has a surface area of from about 500 mm$^2$ to about 800 mm$^2$.

19. The process of claim 12, wherein the liquid comprises two or more polymerizable monomers.

20. The process of claim 12, wherein the polymerization column or mold is further charged with a free-radical polymerization catalyst selected from organic peroxides, percarbonates, peroxycarbonates, peroxydicarbonates, hydroperoxides, alkali metal sulfates, benzoin methyl ether, or a mixture of any two or more thereof.

* * * * *